United States Patent [19]

Burk et al.

[11] 4,049,695

[45] Sept. 20, 1977

[54] 3-((3-TRIFLUOROMETHYL)PHENYL)SUL-FONYL)-2-PROPENENITRILE

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 749,483

[22] Filed: Dec. 10, 1976

[51] Int. Cl.$^2$ .................................................. C07C 121/70
[52] U.S. Cl. .................................. 260/465 G; 424/304
[58] Field of Search ...................................... 260/465 G

[56] References Cited

U.S. PATENT DOCUMENTS

| 3,159,532 | 12/1964 | Heininger et al. | 424/304 |
| 3,541,119 | 11/1970 | Richter et al. | 260/397.6 |
| 3,821,399 | 6/1974 | Richter | 424/304 |

*Primary Examiner*—Dolph H. Torrence
*Attorney, Agent, or Firm*—Theodore Post; C. Kenneth Bjork

[57] ABSTRACT

3-((3-(Trifluoromethyl)phenyl)sulfonyl)-2-propenenitrile. The compound has antimicrobial utility.

1 Claim, No Drawings

3-((3-TRIFLUOROMETHYL)PHENYL)SULFONYL)-2-PROPENENITRILE

DESCRIPTION OF KNOWN PRIOR ART

S. A. Heininger et al., in U.S. Pat. No. 3,159,532, patented Dec. 1, 1964, discloses phenylsulfonyl alkenenitriles which are said to inhibit the growth of microorganisms such as bacteria and fungi. Compounds such as 3-(4-chlorophenylsulfonyl)acrylonitrile and analogs thereof having on the phenyl nucleus other halo or lower alkyl substitution are disclosed. S. U. K. A. Richter, in U.S. Pat. No. 3,541,119, patented Nov. 17, 1970, discloses benzenesulfonylacrylonitrile and homologs and analogs thereof having halo or lower alkyl or p-acetamido substitution on the benzene nucleus. The compounds are said to have bioactive properties. S. U. K. A. Richter, in U.S. Pat. No. 3,821,399, discloses that certain phenylsulfonylacrylonitriles wherein the phenyl moiety has at least one substituent selected from amino, acylamido or nitro and, optionally, a second lower alkyl substituent on the phenyl moiety, prevent the growth of microorganisms.

SUMMARY OF THE INVENTION

The new compound 3-(3-trifluoromethyl)-phenyl)sulfonyl)-2-propenenitrile having the formula

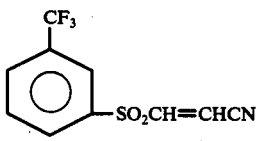

is prepared by mixing together m-trifluoromethylbenzenesulfonyl chloride with excess acrylonitrile, a small proportion of acetonitrile and a catalytic amount of cupric chloride together with triethylamine hydrochloride as catalyst in a cooled, evacuated vessel, submersing the latter in an oil bath at about 110° C to substantial completion of reaction (ca. 3 days), stripping the solvents, and then treating the resulting amber oil with methanol and extracting with methylene chloride. The extract, a mixture of 3-(3-(trifluoromethyl)phenyl )-sulfonyl)-2-propenenitrile and 3-((3-trifluoromethyl)-phenyl)sulfonyl)-2-chloropropanenitrile was treated with excess triethylamine in benzene at a low temperature, by-product triethylamine hydrochloride was filtered off and the solvent was removed to give a white crystalline product, which upon recrystallization from methanol, gave the title product, melting at 79°–80° C.

DESCRIPTION OF SOME PREFERRED EMBODIMENTS

The inventive product has antimicrobial activity. In the conventional in vitro agar Petri dish dilution test for determining bactericidal and fungicidal activity, the compound gave 100% inhibition against the indicated organisms at the following concentrations in parts per million, the tabulated values being indicated as minimum inhibitory concentrations (MIC).

TABLE

| 3-((3-(Trifluoromethyl)phenyl)sulfonyl)-2-propenenitrile | |
|---|---|
| Minimum Inhibitory Concentration, ppm | |
| S. aureus | 5 |
| C. albicans | 50 |
| T. mentagrophytes | 10 |
| K. pneumoniae M-1 Midland Hospital | 50 |
| P. chrysogenum | 50 |
| A. niger | 50 |
| B. subtilis | 5 |
| C. pelliculosa | 10 |
| P. pullulans | 50 |
| S. typhosa | 5 |
| Pseudomonas Sp. Strain 10 | 100 |
| C. ips | 10 |
| Trichoderm Sp. Madison P-42 | 50 |
| S. marcescens NIH | 50 |
| Torulopsis Species | 50 |
| A. fumigatus | 50 |
| C. albicans NIH | 50 |
| E. coli ATCC 11229 | 50 |

The following additional descriptive example further describes the invention and the manner and process of making and using it to enable the art skilled to make and use the same and sets forth the best mode contemplated by the inventors of carrying out the invention.

EXAMPLE 3-((3-(Trifluoromethyl)phenyl)sulfonyl)-2-propenenitrile

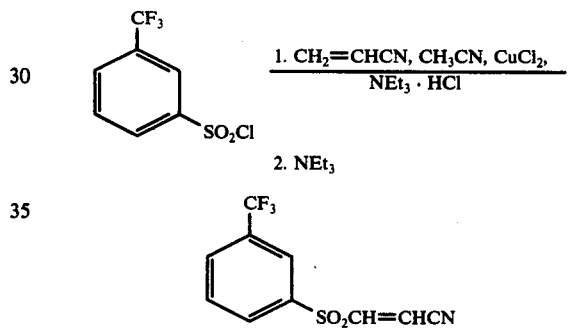

A 12.4 g (0.05 mol) portion of m-trifluoromethylbenzenesulfonyl chloride was introduced into a 100 ml Fisher-Porter reaction vessel along with 5.3 g (0.1 mol) of acrylonitrile, 2 ml of acetonitrile, 0.07 g of cupric chloride and 0.11 g of triethylamine hydrochloride as catalyst. After cooling and evacuation at 2 mm Hg, the vessel was submersed in an oil bath at 110° C for three days. After stripping the solvents, an amber oil was recovered which on treatment with aqueous methanol and extraction with methylene chloride gave 10.0 g of a light amber oil. The extracted oil proved to be a mixture of the 3-arylsulfonyl-2-propenenitrile product and 3-arylsulfonyl-2-chloropropanenitrile. Treatment of this mixture with excess triethylamine in benzene at 10° C, followed by filtration of the amine hydrochloride and removal of solvent, afforded 3.7 g of white crystals upon recrystallization from methanol, m. p. 79°–80° C.

Anal. Calcd. for $C_{10}H_6F_3NO_2S$: C, 46.4; H, 2.3; N, 5.3. Found: C. 46.04; H, 2.3; N, 5.5.

The m-trifluoromethylbenzenesulfonyl chloride starting material was prepared by reacting benzotrifluoride with chloroesulfonic acid in the presence of oleum (65% $SO_3$), according to the method described in Chemical Abtracts 75, 19942d, (1971); German Offen. No. 1,954,448.

What is claimed is:

1. The compound 3-((3-(trifluoromethyl)-phenyl)sulfonyl)-2-propenenitrile.